(12) United States Patent  
Lévesque et al.

(10) Patent No.: US 6,949,380 B1  
(45) Date of Patent: Sep. 27, 2005

(54) TRANSDIFFERENTIATION OF EPIDERMAL BASAL CELLS INTO NEURAL PROGENITOR CELLS, NEURONAL CELLS AND/OR GLIAL CELLS

(75) Inventors: Michel F. Lévesque, Beverly Hills, CA (US); Toomas Neuman, Santa Monica, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/488,491

(22) Filed: Jan. 20, 2000

Related U.S. Application Data

(63) Continuation-in-part of application No. 09/234,332, filed on Jan. 20, 1999, now Pat. No. 6,087,168.

(51) Int. Cl.$^7$ ................................................ C12N 5/00
(52) U.S. Cl. .......................... 435/325; 435/6; 435/375; 435/336; 435/384; 536/24.5
(58) Field of Search .......................... 435/6, 7.21, 91.1, 435/91.31, 91.4, 455, 325, 366, 375; 536/23.1, 24.5; 514/44

(56) References Cited

U.S. PATENT DOCUMENTS

| | | | |
|---|---|---|---|
| 4,560,655 A | 12/1985 | Baker | |
| 5,041,538 A | 8/1991 | Ling et al. | |
| 5,143,842 A | 9/1992 | Ham et al. | |
| 5,182,375 A | 1/1993 | Ling et al. | |
| 5,324,656 A | 6/1994 | Ham et al. | |
| 5,411,883 A | 5/1995 | Boss et al. | |
| 5,589,376 A | 12/1996 | Anderson et al. | |
| 5,670,481 A | 9/1997 | Harland et al. | |
| 5,679,783 A | 10/1997 | De Robertis et al. | |
| 5,753,506 A | 5/1998 | Johe | |
| 5,821,124 A | 10/1998 | Valenzuela et al. | |
| 5,843,775 A | 12/1998 | Valenzuela et al. | |
| 5,846,770 A | 12/1998 | LaVallie et al. | |
| 5,902,785 A | 5/1999 | Hattersley et al. | |
| 5,986,056 A | 11/1999 | La Vallie et al. | |

FOREIGN PATENT DOCUMENTS

WO      WO 97/11095      3/1997

OTHER PUBLICATIONS

Branch, TIBS 23, pp. 45–50, Feb. 1998.*
Flanagan et al., Nature Biotech. 17: 48–52, Jan. 1999.*
Chang et al., Development (Eng), 126(15) p. 3347–57, Aug. 1999.*
Adam, E. et al., *Neuraminic acid specific lectins as markers of early cortical plate neurons*, Int. J. Dev. Neurosci, 11(4):451–60 (Aug. 1993) Abstract Only.
Bellefroid, Eric J. et al., *X–MyT1, a Xenopus C2HC–Type Zinc Finger Protein with a Regulatory Function in Neuronal Differentiation*, Cell, vol. 87, 1191–1202, Dec. 1996.
Brown, T.J., et al. *Characterization of 11 beta–methoxy–16 alpha–[125I] iodoestradial binding: neuronal localization of estrogen–binding sites in the developing rat brain.* Endocrinology, 124(5):2074–88 (May 1989) Abstract Only.
Cassiman, D., et al., *Synaptophysin: A Novel Marker for Human and Rat Hepatic Stellate Cells*, Am. J. Pathol, 155(6):1831–1839 (Dec. 1999) Abstract Only.
Demetriou M., et al., *Fetuin/alpha 2–HS glycoprotein is a transforming growth factor–beta type II receptor mimic and cytokine antagonist*, J. Biol. Chem. , 271(22):12755–61 (May 1996) Abstract Only.
Dziegielewska K.M., et al., *Synthesis of the foetal protein fetuin by early developing neurons in the immature neocortex*, J. Neurocytol, 22(4):266–72 (Apr. 1993). Abstract Only.
Fann, M.J., et al., *Depolarization differentially regulates the effects of bone morphogenetic protein (BMP)–2, BMP–6, and activin A on sympathetic neuronal phenotype*, J. Neurochem, 63(6):2074–9 (Dec. 1994) Abstract Only.
Furuta, Y., et al., *Bone morphogenetic proteins (BMPs) as regulators of dorsal forebrain development*, Development, 124(11):2203–12 (Jun. 1997) Abstract Only.
Guillemot, F., et al., *Dynamic expression of the murine Achaete–Scute homologue Mash–1 in the developing nervous system*, Mech. Dev., 42(3):171–85 (Aug. 1993) Abstract Only.
Hattori, A., et al., *Bone morphogenetic protein–2 promotes survival and differentiation of striatal GABAergic neurons in the absence of glial cell proliferation*, J. Neorochem, 72(6):2264–71 (Jun. 1999) Abstract Only.

(Continued)

Primary Examiner—Sean McGarry
Assistant Examiner—J D Schultz
(74) Attorney, Agent, or Firm—Jones Day (57) ABSTRACT

Disclosed is a method of transdifferentiating an epidermal basal cell into a cell having one or more morphological, physiological and/or immunological features of a neural progenitor, neuronal, or glial cell by culturing a proliferating epidermal basal cell population derived from the skin of a mammalian subject; exposing the epidermal basal cell(s) to an antagonist of bone morphogenetic protein (BMP), such as fetuin, noggin, chordin, gremlin, or follistatin; and growing the cell(s) in the presence of at least one antisense oligonucleotide comprising a segment of a human MSX1 gene and/or a segment of a human HES1 gene, or homologous non-human counterpart of either of these. Also disclosed is a transdifferentiated cell of epidermal origin and cell cultures derived therefrom. In addition, methods of using the inventive transdifferentiated cell(s) and cell cultures to identify a novel nerve growth factor or to screen a potential chemotherapeutic agent by detecting the presence or absence of an effect, in vitro, on a morphological, physiological and/or molecular biological property of the transdifferentiated cell(s) are described, as is a method of using the transdifferentiated cell(s) and cell cultures to screen a potential chemotherapeutic agent to treat a nervous system disorder of genetic origin. A kit useful for practicing the methods is disclosed

25 Claims, 2 Drawing Sheets

OTHER PUBLICATIONS

Hirota Y., et al., *Musashi and seven in absentia downregulate tramtrack through distinct mechanisms in drosophila eye development*, Mech. Dev., 87(1–2):93–101 (Sep. 1999) Abstract Only.

Iantosca, M.R., et al., *Bone morphogenetic proteins–2 and –4 attenuate apoptosis in a cerebellar primitive neuroectodermal tumor cell line*, J. Neurosci Res., 56(3):248–58 (May 1999) Abstract Only.

Ishibashi, M., et al., *Targeted disruption of mammalian hairy and Enhancer of split homolog–1 (HES–1) leads to up–regulation of neural helix–loop–helix factors, premature neurogenesis, and severe neural tube defects*, Genes & Development, 9:3136–3148 (1995).

Ishibashi, M., et al., *Persistent expression of helix–loop–helix factor HES–1 prevents mammalian neural differentiation in the central nervous system*, The EMBO Journal, vol. 13, No. 8, pp. 1799–1805 (1994).

Ishizeki, K., et al., *Sequential synthesis of cartilage and bone marker proteins during transdifferentiation of mouse Meckel's cartilage chondrocytes in vitro*, Int. J. Dev. Biol., 41(1):83–9 (Feb. 1997) Abstract Only.

Iwasaki, S., et al., *Characterization of the bone morphogenetic protein–2 as a neurotrophic factor. Induction of neuronal differentiation of PC12 cells in the absence of mitogen–activated protein kinase activation*, J. Biol. Chem. 271(29):17360–5 (Jul. 1996) Abstract Only.

Kalyani, A.J., et al., *Spinal cord neuronal precursors generate multiple neuronal phenotypes in culture*, J. Neurosci, 18(19):7856–68 (Oct. 1998) Abstract Only.

Kitchener, P.D., et al., *Fetuin in neurons of the retina and cerebellum during fetal and postnatal development of the rat*, Int. J. Dev. Neurosci, 17(1):21–30 (Feb. 1999) Abstract Only.

Lee, Jacqueline E., et al., *Conversion of Xenopus Ectoderm into Neurons by NeuroD, a Basic Helix–Loop–Helix Protein*, Science, vol. 268, pp. 836–844 (May 1995).

Lee, K.J., et al., *Neuronal patterning by BMPs: a requirement for GDF7 in the generation of a discrete class of commissural interneurons in the mouse spinal cord*, Genes Dev. 12(21):3394–407 (Nov. 1998) Abstract Only.

Lee, M.H., et al., *Transient upregulation of CBFA1 in response to bone morphogenetic protein–2 and transforming growth factor beta1 in C2C12 myogenic cells coincides with suppression of the myogenic phenotype but is not sufficient for osteoblast differentiation*, J. Cell Biochem. 73(1):114–25 (Apr. 1999) Abstract Only.

Lein, P., et al., *Osteogenic protein–1 induces dendritic growth in rat sympathetic neurons*, Neuron, 15(3):597–605 (Sep. 1995) Abstract Only.

Ma, Qiufu, et al., *Identification of neurogenin, a Vertebrate Neuronal Determination Gene*, Cell, vol. 87, 43–52 (Oct. 4, 1996).

Mayer–Proschel, M., et al., *Isolation of lineage–restricted neuronal precursors from multipotent neuroepithelial stem cells*, Neuron, 19(4):773–85 (Oct. 1997) Abstract Only.

McCormick, Mary B., et al., *neuroD2 and neuroD3: Distinct Expression Patterns and Transcriptional Activation Potentials within the neuroD Gene Family*, Molecular and Cellular Biology, vol. 16, No. 10, p. 5792–5800 (Oct. 1996).

Merino, R., et al., *The BMP antagonist Gremlin regulates outgrowth, chondrogenesis and programmed cell death in the developing limb*, Development, 126(23):5515–5522 (1999) Abstract Only.

Murray, S.S., et al., *Bone morphogenetic protein inhibits differentiation and affects expression of helix–loop–helix regulatory molecules in myoblastic cells*, J. Cell Biochem, 53(1):51–60 (Sep. 1993) Abstract Only.

Nagata, T., et al., *Structure, backbone dynamics and interactions with RNA of the C–terminal RNA–binding domain of a mouse neural RNA–binding protein, Musashi 1*, J. Mol. Biol., 287(2):315–30 (Mar. 1999) Abstract Only.

Nikaido, M. et al., *In vivo analysis using variants of zebrafish BMPR–IA: range of action and involvement of BMP in ectoderm patterning*, Development, 126(1):181–90 (Jan. 1999). Abstract Only.

Nakata, Katsunori, et al., *Xenopus Zic3, a primary regulator both in neural and neural crest development*, Proc. Natl. Acad. Sci. USA, vol. 94, pp. 11980–11985 (Oct. 1997).

Park, J.K., et al., *Bipotent cortical progenitor cells process conflicting cues for neurons and glia in a hierarchical manner*, J. Neurosci. 19(23):10383–9 (Dec. 1999) Abstract Only.

Pera, E. et al., *Ectodermal patterning in the avian embryo: epidermis versus neural plate*, Development, 126(1):63–73 (Jan. 1999) Abstract Only.

Rayl, A.J.S., *Transplanted Neurons Migrate Widely in the Adult Brain*, The Scientist, vol. 13, #18, p. 33 (Sep. 13, 1999).

Renoncourt, Y., et al., *Neurons derived in vitro from ES cells express homeoproteins characteristic of motoneurons and interneurons*, Mech. Dev., 79(1–2):185–97 (Dec. 1998) Abstract Only.

Sang, Q., et al., *Innervation of the esophagus in mice that lack MASH1*, J. Comp. Neurol, 408(1):1–10 (May 1999) Abstract Only.

Sasai, Y., *Identifying the missing links: genes that connect neural induction and primary neurogenesis in vertebrate embryos*, Neuron, vol. 21, No. 3, pp. 455–458 (Sep. 1998).

Sato, K., et al., *Cartilaginous transdifferentiation of rat tenosynovial cells under the influence of bone morphogenetic protein in tissue culture*, Clin. Orthop., (236):233–9 (Nov. 1988) Abstract Only.

Sela–Donenfeld, D., et al., *Regulation of the onset of neural crest migration by coordinated activity of BMP4 and noggin in the dorsal neural tube*, Development, 126(21):4749–62 (Nov. 1999) Abstract Only.

Shou, J., et al., *BMPs inhibit neurogenesis by a mechanism involving degradation of a transcription factor*, Nat. Neurosci, 2(4):339–45 (Apr. 1999) Abstract Only.

Stemple, D.L., et al., *Neural stem cells are blasting off*, Neuron, vol. 18, No. 1, pp. 1–4 (Jan. 1997).

Suzuki, Atsushi, et al., *Xenopus msx1 mediates epidermal induction and neural inhibition by BMP4*, Development, vol. 124, pp. 3037–3044 (1997).

Tanabe. Yasuto, et al., *Diversity and Pattern in the Developing Spinal Cord*, Science, vol. 274, pp. 1115–1123, (Nov. 15, 1996).

Weinstein, D.C., et al., *Epidermal induction and inhibition of neural fate by translation initiation factor 4AIII*, Development, 124(21):4235–42 (Nov. 1997) Abstract Only.

Wichterle, H., et al., *Young neurons from medial ganglionic eminence disperse in adult and embryonic brain*, Nat Neurosci, 2(5):461–6 (May 1999) Abstract Only.

Wichterle H., et al., *Direct evidence for homotypic, glia–independent neuronal migration*, Neuron, 18(5):779–91 (May 1997) Abstract Only.

Wickelgren, Ingrid, *Teaching the Spinal Cord to Walk*, Science, vol. 279, pp. 319–321 (Jan. 16, 1998).

Zhu, G., et al., *Sonic hedgehog and BMP2 exert opposing actions on proliferation and differentiation of embryonic neural progenitor cells*, Dev. Biol., 215(1):118–29 (Nov. 1999) Abstract Only.

Zuniga, A., et al., *Signal relay by BMP antagonism controls the SHH/FGF4 feedback loop in vertebrate limb buds*, Nature, 401(6753):598–602 (Oct. 1999) Abstract Only.

XP–002194251—Honoré. Éric. et al., *L'induction neurale chez les vertébrés: le cerveau par défaut*, Médecine/Science, vol. 13, No. 2, pp. 192–200 (Feb. 1997) (English summary attached), summary only considered.

XP–002194263—Nagai, Takeharu, et al., *The Expression of the Mouse Zic1, Zic2, and Zic3 Gene Suggests an Essential Role for Zic Genes in Body Pattern Formation*, Developmental Biology, vol. 182, pp. 299–313 (1997). Article No. DB968449.

XP–002194264—Kim, Peter et al., *XATH–1, A Vertebrate Homolog of Drosophila atonal, Induces Neuronal Differentiation within Ectodermal Progenitors*, Developmental Biology, vol. 187, pp. 1–12 (1997). Article No. DB978572.

Streit, Andrea et al., *Neural Induction, a bird's eye view*, TIG, vol. 15, No. 1, pp. 20–24 (Jan. 1999).

European Search Report, Application No. 00101100, mailed Apr. 10, 2002.

European Search Report, Application No. 00101101, mailed Apr. 10, 2002.

* cited by examiner

TRANSDIFFERENTIATION OF EPIDERMAL BASAL CELLS INTO NEURAL PROGENITOR CELLS, NEURONAL CELLS AND/OR GLIAL CELLS

This application is a continuation-in-part of U.S. patent application Ser. No. 09/234,332, filed on Jan. 20, 1999, which issued as U.S. Pat. No. 6,087,168 on Jul. 11, 2000.

BACKGROUND OF THE INVENTION

Throughout the application various publications are referenced in parentheses. The disclosures of these publications in their entireties are hereby incorporated by reference in the application in order to more fully describe the state of the art to which this invention pertains.

1. Field of the Invention

The present invention is related to the medical arts, particularly to the field of neural tissue regeneration.

2. Discussion of the Related Art

The human nervous system comprises highly diverse cell types that make specific interconnections with one another. The nervous system includes the peripheral nerves and the central nervous system. The central nervous system includes the brain, cranial nerves, and spinal cord. Once damaged, the central nervous system of the adult has limited potential for structural self-repair. The general inability of the adult to generate new neurons (excitable cells specialized for the transmission of electrical signals from one part of the body to another) typically prevents the regeneration of neural tissues. This limitation has hindered the development of therapies for neurological injury, for example from stroke or physical trauma, or for degenerative diseases, such as Huntington disease, Alzheimer disease, and Parkinsonism. The moderate success of fetal tissue transplantation therapy for Parkinsonism suggest that cell replacement therapy can be a valuable treatment for neurological injury and degeneration.

Thus, there is a long felt need in the biomedical field for a method of generating neurons for use in the treatment of various neurological traumas, diseases, disorders, or maladies via the direct transfer of neuronal cells in a cell replacement therapy approach.

A gene therapy approach, on the other hand, is required to treat other types of nervous system disorders. Because the brain is protected by a blood-brain barrier that effectively blocks the flow of large molecules into the brain, peripheral injection of growth factor drugs, or other potentially therapeutic gene products, is ineffective. Thus, a major challenge facing the biotechnology industry is to find an efficient mechanism for delivering gene therapy products, directly to the brain, so as to treat neurological disorders on the molecular level. In this regard, a renewable source of human neural cells could serve as a vehicle to deliver gene therapy products to the brain and the rest of the central nervous system.

Until recently, the only source of donor material for these promising therapies was fetal tissue. However, the use of fetal tissue presents significant ethical and technical problems, including the limited availability of fetal tissue, the possible immuno-rejection of donor material by the recipient, and the risk of disease transmission by donor material.

Several attempts have been made to address the shortage of donor material by culturing neural progenitor cells, or neural stem cells. For example, Boss et. al taught a method for isolation and proliferation of neural progenitor cells directed to growth, storage, production and implantation of the proliferated donor cells. (Boss et. al, Proliferated Neuron Progenitor Cell Product and Process, U.S. Pat. No. 5,411,883). Anderson et. al taught a method for isolation and clonal propagation of donor mammalian neural crest stem cells capable of self renewal and differentiation into neural or glial cells. (Anderson et. al, Mammalian Neural Crest Stem Cells, U.S. Pat. No. 5,589,376). Johe taught a method for isolation, propagation and directed differentiation of stem cells from the central nervous system of embryonic and adult mammalian donors. (Johe, Isolation Propagation and Directed Differentiation of Stem Cells from Embryonic and Adult Central Nervous System of Mammals, U.S. Pat. No. 5,753,506).

Neural progenitor cells normally develop from embryonic ectodermal tissue. Bone Morphogenetic Protein (BMP) is a family of repressors that prevents ectoderm from developing into its default state of neural tissue and induces the development instead of epidermal tissue. (Y. Tanabe & T. M. Jessell, *Diversity and Pattern in the Developing Spinal Cord*, Science 274:1115 [1996]; Y. Sasai, *Identifying the missing links: genes that connect neuronal induction and primary neurogenesis in vertebrate embryos*, Neuron 21:455–58 [1998]; Y. Furuta et al., *Bone morphogenetic proteins (BMPs) as regulators of dorsal forebrain development*, Development 124(11):2203–2212 [1997]). BMP 2 and BMP 4 induce epidermal differentiation. (E. Pera et al., *Ectodermal Patterning in the Avian Embryo: Epidermis Versus Neural Plate*, Development 126:63 [1999]).

BMP's can also induce cartilage formation. Hattersley et al. showed that adding BMP 13 to a cell line derived from mouse limb buds leads to the formation of chondroblast-like cells and taught a method for using BMP 13 to induce articular cartilage formation at the site of congenital or trauma induced damage and for using BMP 9 to maintain cartilage. (Hattersley et al., Cartilage Induction by Bone Morphogenetic Proteins, U.S. Pat. No. 5,902,785).

BMP signal transduction appears to be mediated by msx1, which is an immediate early response gene involved in epidermal induction and inhibition of neuronal differentiation. When Suzuki et al. injected BMP RNA into *Xenopus* embryos, they detected msx1 RNA production; when they injected msx1 RNA, the embryos lost neuronal structures such as eyes. (Suzuki et al., *Xenopus msx1 Mediates Epidermal Induction and Neural Inhibition by BMP4*, Development 124:3037 [1997]). When msx1 was added directly to dissociated ectodermal cells, epidermal development was up-regulated and neural development was down-regulated. Similarly in humans, BMP growth factors induce expression of the homeodomain transcription factor MSX1 in ectodermal cells. Once MSX1 is expressed, induction of the neuronal determination genes is simultaneously suppressed and neuronal differentiation is inhibited.

BMP seems to down-regulate neural development through at least two mechanisms: proteolysis of MASH1 protein and inhibition of Zic3 production. Exposure of neural progenitor cells to BMP triggered a rapid loss of MASH1 protein, a transcription factor that is homologous to the *Drosophila* Achaete-Scute Complex (ASH1) and required for the production of olfactory receptor neurons. (Shou et al., *BMPs Inhibit Neurogenesis by a Mechanism Involving Degradation of a Transcription Factor*, Nat. Neurosci. 2:339 [1999]). Micro-injection of the dominant negative form of the BMP receptor, an inhibitor of BMP, into *Xenopus* embryos induced production of Zic3, a protein that augments neural development. (Nakata et al. *Xenopus Zic3, a Primary Regulator Both in Neural and Neural Crest Development*, Proc. Natl. Acad. Sci. 94: 11980 [1997]).

Antagonists of BMP signal transduction activity include fetuin glycoprotein, also known as α2-HS glycoprotein in humans, and the DAN family of BMP antagonists, such as noggin, chordin, follistatin, and gremlin. R. Merino et al., *The BMP antagonist Gremlin regulates outgrowth, chondrogenesis and programmed cell death in the developing limb*, Development 126(23):5515–22 [1999]; D. Sela-Donnenfeld and C. Kalcheim, *Regulation of the onset of neural crest migration by coordinated activity of BMP4 and noggin in the dorsal neural tube*, Development 126(21): 4749–62 [1999]). For example, Demetriou et al. showed that fetuin blocks osteogenesis, a function promoted by BMP, in a culture of rat bone marrow cells and that a fetuin derived peptide binds BMP 2. (M. Demetriou et al., *Fetuin/Alpha2-HS Glycoprotein is a Transforming Growth Factor-Beta Type II Receptor Mimic and Cytokine Antagonist*, J. Biol. Chem. 271:12755–61 [1996]). During embryonic and early postnatal development, Fetuin was shown to be present in a sub-population of cells in the retinal ganglion cell layer, the neuroblastic layer, and portions of the developing cerebellum. (Kitchener et al., *Fetuin in Neurons of the Retina and Cerebellum During Fetal and Postnatal Development of the Rat*, Int. J. Dev. Neurosci. 17: 21 ([1999]).

Fetuin has been used as an additive in serum free media. Ham et al. taught the use of fetuin as an additive in serum free media for the growth of normal human muscle satellite cells directed at transplantation to the muscles of patients afflicted with muscle degenerative diseases. (Ham et al., Media for Normal Human Muscle Satellite Cells, U.S. Pat. No. 5,143,842; Ham et al., Media for Normal Human Muscle Satellite Cells, U.S. Pat. No. 25 5,324,656). Baker taught the use of fetuin as an additive in a defined serum free media that is capable of growing a wide range of cell suspensions and monolayers. (Baker, Serum-Free Cell Culture Medium and Process for Making Same, U.S. Pat. No. 4,560,655).

Other factors beside BMP appear to be involved in regulating neural differentiation. Ishibashi et al. demonstrated that persistent expression of Hairy and Enhancer of Split Homolog-1 (HES1) severely perturbs neuronal and glial differentiation. They infected the lateral ventricles of the brains of embryonic mice with a retrovirus that produced HES1. This led to failed migration and differentiation in the developing cells that were infected. (Ishibashi et al., *Persistent Expression of Helix-Loop-Helix Factor HES-1 Prevents Mammalian Neural Differentiation in the Central Nervous System*, The EMBO Journal 13: 1799 [1994]). Ishibashi et al. also disrupted the HES1 gene in mice and observed earlier than usual neurogenesis. They concluded that HES1 controls the timing of neurogenesis. (Ishibashi et al., *Targeted Disruption of Mammalian Hairy and Enhancer of Split Homolog-1 (HES-1) Leads to Up-Regulation of Neural Helix-Loop-Helix Factors, Premature Neurogenesis, and Severe Neural Tube Defects*, Genes & Development 9: 3136 [1995]). In addition retinoids, such as retinoic acid, may play a role in inducing the differentiation of some neural cell populations. (e.g., Y. Renoncourt et al., *Neurons derived in vitro from ES cells express homeoproteins characteristic of motoneurons and interneurons*, Mechanisms of Development 79:185–97 ([1998]).

Thus, the differentiation of neuronal tissue involves the interaction of numerous positive and negative regulatory molecules. In response to developmental signals within each cell and its surrounding microenvironment, every neuronal population expresses a specific set of neural markers, neurotransmitters, and receptors. As neural progenitor cells differentiate into other neuronal cell types in response to physiological signals in the microenvironment, the set that is expressed will be different. (E.g., see D. L. Stemple and N. K. Mahanthappa, *Neural stem cells are blasting off*, Neuron 18:1–4 [1997]; Y. Renoncourt et al., *Neurons derived in vitro from ES cells express homeoproteins characteristic of motoneurons and interneurons*, Mechanisms of Development 79:185–97 [1998]; A. J. Kalyani et al, Spinal cord neuronal precursors generate multiple neuronal phenotypes in culture, J. Neurosci. 18(19):7856–68 ([1998]). Each neuronal cell type is characterized by several criteria including morphology (e.g., long processes or neurites), expression of a set of neural-specific markers (e.g., neurofilament M, neural-specific tubulin, neural-specific enolase, microtubule associated protein 2, and others), synthesis of neurotransmitters (e.g., dopamine or expression of tyrosine hydroxylase, the key enzyme in dopamine synthesis), and membrane excitability.

One of the central principles of modem neurobiology is that after differentiation each of the major projection neurons, if not all neuronal cell types, requires for its survival specific cytokines, i.e., neurotrophic or nerve growth factors, to reach their target neuronal cells. Neuropathies in many diseases may be caused by, or involve lack of, such nerve growth factors. These nerve growth factors represent the next generation of preventative and therapeutic drugs for nervous system disorders. Most of the growth factors known so far in the nervous system were discovered by their effects on peripheral nerves and these most likely represent a very minor fraction of existing growth factors in the brain. Search for growth factors from the brain has been difficult mainly because particular neuronal cell types are difficult to isolate from the brain and maintain in defined culture conditions.

Due to this limitation, drug discovery by traditional pharmacology directed to the central nervous system has been performed using whole brain homogenate and animals. These studies mostly produced analogs of neurotransmitters with broad actions and side effects. But as more and more neurotransmitter receptors and signal transducing proteins have been identified from the brain, it is becoming clear that the dogma of one neurotransmitter activating one receptor is an over-simplification. Most receptor complexes in neurons are composed of protein subunits encoded by several genes and each gene synthesizes many different variations of the protein. These variations result in a wide range of possible receptor combinations, and not a single receptor that can interact with a neurotransmitter. Consequently, a range of signal output may be produced by a single neurotransmitter action. The specific signal effected by a neurotransmitter on a neuron, then, depends on which receptor complex is produced by the cell. Thus, cellular diversity must parallel the molecular diversity and constitute a major structural element underlying the complexity of brain function, and a source of diverse neuronal cell types that can be cultured for drug screening purposes is needed.

Therefore, there remains a need in the field of neurological research and applied neurobiology for a renewable non-fetal source of neural progenitor cells and cells having characteristics specifically associated with neuronal or glial cell types, for use in research, cell therapy, or gene therapy. These and other benefits the present invention provides as described herein.

SUMMARY OF THE INVENTION

The present invention relates to a method of transdifferentiating an epidermal basal cell into a cell having one or more morphological, physiological and/or immunological feature(s) of a neural progenitor cell, a neuronal cell, or a glial cell. The method involves culturing a proliferating epidermal basal cell population derived from the skin of a mammalian subject, exposing the epidermal basal cell(s) to an amount of an antagonist of bone morphogenetic protein (BMP) effective to antagonize endogenous BMP signal transduction activity, and growing the cell(s) in the presence of at least one antisense oligonucleotide comprising a segment of a human MSX1 gene or a segment of a human HES1 gene, or homologous non-human counterpart of either of these, such that expression of functional gene product of MSX1 or HES1 is suppressed. By these steps the cell is transdifferentiated into a cell having one or more morphological, physiological and/or immunological feature(s) of a neural progenitor cell, neuronal cell, or glial cell.

The present invention also relates to a transdifferentiated cell(s) of epidermal origin. The inventive transdifferentiated cell is a cell of epidermal basal cell origin that displays one or more morphological, physiological and/or immunological feature(s) of a neural progenitor, neuronal, or glial cell. The physiological and/or immunological feature can be, but is not limited to, expression of one or more marker(s) specific to a neural progenitor, neuronal, or glial cell, by which the transdifferentiated cell is recognized as a neural progenitor, neuronal or neuron-like cell, or a glial or glial-like cell.

The present invention also relates to cell cultures derived from the inventive transdifferentiated cell(s).

The present invention is also directed to a method of delivering locally secretable regulatory factors using the inventive transdifferentiated cells, which are genetically modified, before or after their transdifferentiation, with an expression vector comprising a DNA encoding a preselected secretable regulatory factor or a biochemical precursor thereof, or a DNA encoding an enzyme that catalyzes the synthesis of either of these. The genetically modified, transdifferentiated cells are implanted into a mammalian subject, and the implanted cells secrete the locally secretable regulatory factor.

The present invention also relates to method of using the inventive transdifferentiated cell(s) to identify a novel nerve growth factor or potential chemotherapeutic agent. The methods involve transdifferentiating a population of proliferating epidermal basal cells into neuronal progenitor cells, neuronal cells, or glial cells; culturing the transdifferentiated cells; exposing the cultured cells, in vitro, to a potential nerve growth factor (i.e., neurotrophin or neurotrophic factor) and/or potential chemotherapeutic agent; and detecting the presence or absence of an effect of the potential nerve growth factor and/or potential chemotherapeutic agent on the survival of the cells or on a morphological or electrophysiological characteristic and/or molecular biological property of the cells. The presence of an effect altering cell survival, a morphological or electrophysiological characteristic and/or a molecular biological property of the cells indicates the activity of the potential nerve growth factor and/or potential chemotherapeutic agent.

The present invention also relates to a method of using the inventive transdifferentiated cell(s) to screen a potential chemotherapeutic agent to treat a nervous system disorder of genetic origin. In the method the epidermal basal cells are derived from a human subject having a particular nervous system disorder of genetic origin. The cells are transdifferentiated in accordance with the inventive method. The transdifferentiated cells are cultured and exposed, in vitro, to a potential chemotherapeutic agent. The method involves detecting the presence or absence of an effect of the potential chemotherapeutic agent on the survival of the cells or on a morphological or electrophysiological characteristic and/or molecular biological property of said cells. An effect altering cell survival, a morphological or electrophysiological characteristic and/or a molecular biological property of the cells indicates the activity of the chemotherapeutic agent.

The present invention is also related to a kit for transdifferentiating an epidermal basal cell into a cell having one or more morphological, physiological and/or immunological feature(s) of a neural progenitor, neuronal, or glial cell. The kit is useful for practicing the inventive methods.

These and other advantages and features of the present invention will be described more fully in a detailed description of the preferred embodiments which follows. In further describing the invention, the disclosures of related application U.S. Ser. No. 09/234,332 are incorporated by reference.

BRIEF DESCRIPTION OF THE FIGURES

FIG. 1 is a micrograph showing transdifferentiation of epidermal basal cells into Neurofilament-M expressing neuronal cells.

FIG. 2 shows the effect of fetuin concentration on the transdifferentiation of epidermal basal cells. The epidermal basal cells were separated from terminally differentiated keratinocytes and cultured in the presence of HES1 and MSX1 antisense oligonucleotides and fetuin for three days, then an additional three days in the presence of fetuin and all-trans retinoic acid and BDNF, after which they were incubated in fresh growth medium containing all-trans retinoic acid and BDNF for an additional four days. They were then immunostained to detect Neurofilament M expression.

DETAILED DESCRIPTION OF THE PREFERRED EMBODIMENTS

The present invention relates to a method of transdifferentiating an epidermal basal cell into a cell having one or more morphological, physiological and/or immunological feature(s) of a neural progenitor, neuronal, or glial cell. The method involves culturing a proliferating epidermal basal cell population comprising one or more epidermal basal cell(s) derived from the skin of a mammalian subject; exposing the cell(s) to an amount of an antagonist of bone morphogenetic protein (BMP) effective to antagonize endogenous BMP signal transduction activity relative to a control minus the BMP antagonist; and growing the cell(s) in the presence of at least one antisense oligonucleotide comprising a segment of a human MSX1 gene or a segment of a human HES1 gene, or homologous non-human counterpart of either of these, in an amount effective to suppress the expression of functional gene product(s) of MSX1 and/or HES1, i.e., translatable MSX1 and/or HES1 MRNA transcript(s) and/or active MSX1 and/or HES1 protein, in comparison with a control minus the antisense oligionucleotides.

The inventive method results in the cell being transdifferentiated into a cell having one or more morphological, physiological and/or immunological features of a neural progenitor, neuronal or glial cell. Morphological features include, for example, neurite-like process(es) at least about 50 micrometers in length, characteristic of neuronal cells. Physiological and or immunological features include expression of one or more specific markers and/or characteristic physiological responses to neural growth factors and other cytokines. Electrochemical characteristics of the cells, or particularly the cell membranes, are also included among physiological features, as are production and secretion by the transdifferentiated cells of regulatory factors such as dopamine or Y-aminobutyric acid (GABA), characteristic of various neuronal cell types.

In accordance with the inventive method, a proliferating epidermal basal cell population is cultured. The cells of the proliferating epidermal basal cell population are derived from any mammalian subject, including a human subject. The cell(s) can be derived directly from a tissue sample resulting from a surgical procedure such as a skin biopsy of the subject, or can be derived indirectly from cultured or stored epidermal basal cells of the subject.

Epidermal basal cells in a skin tissue sample or in a cultured mixed population of basal and keratnized non-basal epidermal cells, are preferably separated from the terminally differentiated keratinized epidermal cells by exposing the mixed cell population to a calcium-free growth medium. For purposes of the present invention, a calcium-free medium contains less than $10^{-6}$ M calcium cations ($Ca^{2+}$). Low calcium caton concentration results in the stripping of the keratin-forming upper epidermal layers from the basal cells. (E.g., P. K. Jensen and L. Bolund, *Low $Ca^{2+}$ stripping of differentiating cell layers in human epidermal cultures: an invitro model of epidermal regeneration*, Experimental Cell Research 175:63–73 [1988]). The basal cells are then physically separated, selected or isolated from the keratinized cells by any convenient method, such as aspiration or decantation. Calcium cations are required to support development of keratinocytes (skin cells) from basal cells, and returning calcium to the growth medium results in rapid basal cell proliferation in the dedifferentiated cell population (Jensen and Bolund [1988]), and, thus, a proliferating epidermal basal cell population is cultured. Beyond this, it is not necessary to do a dedifferentiating step with respect to individual epidermal basal cell(s) after they are separated, isolated, or selected from the differentiated keratinized cells.

The cells of the resulting cultured proliferating epidermal basal cell population are then exposed to an amount of an antagonist of bone morphogenetic protein (BMP) effective to antagonize (i.e., suppress, prevent, reduce or inhibit) endogenous BMP signal transduction activity. Preferably, exposing the cell(s) to an effective amount of the antagonist of BMP is achieved by aseptically aspirating or decanting the old culture medium and replacing it with fresh culture medium containing a concentration of the antagonist between about $10^{-6}$ M and about $10^{-4}$ M, most preferably between about $5\times10^{-5}$ M and about $5\times10^{-5}$ M, thereafter incubating the cells for several days, preferably a minimum of about three days.

For purposes of the present invention a BMP antagonist is an agent that binds with a BMP molecule (such as but not limited to, BMP2, BMP4, BMP6, or BMP7) to form a complex that prevents or inhibits binding of the BMP molecule by BMP receptors on mammalian cell surfaces, or an agent that binds the BMP receptors, which results in suppression, prevention, reduction, or inhibition of BMP signal transduction. Alternatively, the BMP antagonist is a specific antisense oligonucleotide or ribozyme that prevents or inhibits the expression of functional gene product of a BMP receptor gene or prevents or inhibits the expression of a gene defining a trans-acting constituent of the BMP signaling pathway.

The BMP antagonist can be from any mammalian source, homologous or heterologous to the species from which the epidermal basal(s) derive, or from an avian source. For example, bovine fetuin is useful and conveniently obtained, but other forms including human, porcine, ovine, equine, or avian forms, such as chicken, turkey or duck fetuin can also be used. BMP antagonists, such as noggin, chordin, follistatin, and gremlin are also available to the skilled artisan. (E.g., Valenzuela et al., Human dorsal tissue affecting factor (noggin) and nucleic acid encoding same, U.S. Pat. No. 5,843,775; Harland et al., U.S. Pat. No. 5,670,481; Ling et al., Mammalian follistatin, U.S. Pat. No. 5,041,538; Ling et al., DNA encoding follistatin, U.S. Pat. No. 5,182,375; De Robertis et al., DNA encoding a tissue differentiation affecting factor, U.S. Pat. No. 5,679,783; LaVallie et al., DNA molecules encoding human chordin, U.S. Pat. No. 5,846,770; LaVallie et al., Chordin compositions, U.S. Pat. No. 5,986,056; R. Merino et al., Development 126(23): 5515–22 [1999]); D. Sela-Donnenfeld and C. Kalcheim, Development 126(21):4749–62 [1999]). Alternatively, a synthetic or recombinant analog of a naturally occurring BMP antagonist is also useful in practicing the method. However, sonic hedgehog, or fragments thereof, which are not known to interact with a BMP protein or BMP receptor, are excluded from among useful BMP antagonists in accordance with the inventive method.

Next, the proliferating basal cell(s) are grown in the presence of at least one antisense oligonucleotide comprising a nucleotide sequence of a segment of a human MSX1 gene and/or a nucleotide sequence of a segment of a human HES1 gene, or homologous non-human counterpart of either of these, in an amount sufficient to suppress the expression of functional gene product of MSX1 or HES1. A sufficient amount of antisense oligonucleotides directed to suppressing transcription of both MSX1 and HES1 is a concentration in the medium of about 5 to 10 $\mu$M each. Examples of useful antisense oligonucleotide sequences include the following human MSX1 antisense oligonucleotide sequences:

5'-GACACCGAGTGGCAAAGAAGTCATGTC-3' (first methionine) (MSX1-1; SEQ. ID. NO.:1) or 5'-CGGCTTCCTGTGGTCGGCCATGAG-3' (third methionine) (MSX1-2; SEQ. ID. NO.:2); and two antisense oligonucleotides corresponding to the human HES1 open reading frame 5' sequence:

5'-ACCGGGGACGAGGAATTTCTCCATTATATCAGC-3' (HES1-1; SEQ. ID. NO.:3) or HES1 open reading frame middle sequence 2:

5'-CACGGAGGTGCCGCTGTTGCTGGGCTGGTGTG-GTGTAGAC-3' (HES1-2; SEQ. ID. NO.:4). Other oligonucleotide sequences are also useful as long as they will hybridize to nucleic acids comprising at least a segment of a human or homologous non-human MSX1 gene (e.g., GenBank Accession Nos. M97676 [human]; NM 002448 [human]; X62097 [chicken]; D82577.1 [Ambystoma mexicanum]) or at least a segment of an HES1 gene (e.g., GenBank Accession Nos. Y07572 [human]; Q04666 [rat]; P35428 [mouse ]; AB019516 [newt]; AB016222 [*Saccharomyces pombe*]; U03914 [*Saccharomyces cerevisiae*]), preventing expression of functional MSX1 and/or HES1 gene products by targeting (i.e., hybridizing with) MSX1 or HES1 nucleic acids.

Exposure to the antisense oligonucleotides is for a period long enough for MSX1 and/or HES1 proteins pre-existing in the cells to be degraded. For particular proteins with a relatively short half-life, the exposure period necessary is only a matter of hours to one day. Proteins with relatively long half-life require longer treatments with antisense oligonucleotides. An exposure period of about two to three days generally suffices.

Preferably, one or more nucleotide residues of the antisense oligonucleotides is thio-modified by known synthetic methods, used by the practitioner or by a commercial or other supplier, to increase the stability of the oligonucleotides in the culture media and in the cells. (E.g., L. Bellon et al., 4'-*Thio-oligo-beta-D-ribonucleotides: synthesis is of beta-4'-thio-oligouridylates, nuclease resistance, base pairing properties, and interaction with HIV-1 reverse transcriptase*, Nucleic Acids Res. 21(7):1587–93 [1993]; C. Leydieretal., 4'-*Thio-RNA: synthesis of mixed base 4'-thio-oligoribonucleotides, nuclease resistance, and base pairing properties with complementary single and double strand*, Antisense Res. Dev. 5(3):167–74 [1995]).

The further course of development of the transdifferentiated cells depends on the in situ environmental cues to which they are exposed, whether in vitro, or implanted in vivo. Optionally, the transdifferentiated cell(s) are grown in a medium including a retinoid compound, such as retinoic acid or Vitamin A, and optionally a nerve growth factor or neurotrophin, such as brain-derived neurotrophic factor (BDNF), ciliary neurotrophic factor (CNTF), platelet-derived growth factor (PDGF), nerve growth factor (NGF), neurotrophin (NT)-3, neurotrophin (NT)-4, or sonic hedgehog (Shh), and/or functional fragments of any of these. For example, treating newly formed neuronal cells with all-trans retinoic acid and BDNF results in development of GABAergic neurons or neuron-like cells (that express Neurofilament M), whereas treatment with glial-conditioned media and sonic hedgehog aminoterminal peptide (Shh-N) results in development of mostly dopaminergic neuronal cells. Treatment with Shh-N promotes the differentiation of neuronal and oligodendroglial species from nestin-immunoreactive cells (uncommitted neural progenitor cells) and inhibits the antiproliferative, astroglial-inductive, oligodendroglial-suppressive effects of BMP2. (E.g., G. Zhu et al., *Sonic hedgehog and BMP2 exert opposing actions on proliferation and differentiation of embryonic neural progenitor cells*, Dev. Biol. 21591):118–29 [1999]). This plasticity in response to the environmental cues allows the cells to maintain neuronal differentiation in vitro or in situ, when implanted into the mammalian subject, without the further addition of antisense oligonucleotides.

In accordance with the method, expression of any neural progenitor-specific, neural-specific, and/or glial specific marker is detected by conventional biochemical or immunochemical means. Preferably, immunochemical means are employed, such as, but not limited to, enzyme-linked immunosorbent assay ELISA), immunofluorescent assay (IFA), immunoelectrophoresis, immunochromatographic assay or immunohistochemical staining. These methods employ marker-specific polyclonal or monoclonal antibodies or antibody fragments, for example Fab, Fab', F(ab')$_2$, or F(v) fragments, that selectively bind any of various neural progenitor, neuronal or glial cell antigens. Antibodies targeting individual specific markers are commercially available and are conveniently used as recommended by the antibody manufacturers. Markers specific to neural progenitor, neuronal, or glial cells include antigenic molecules that indicate expression of, for example, nestin, neural RNA-binding protein Musashi, neurofilament M (NF-M; Sigma, Inc.), neural-specific tubulin (Sigma, Inc.), neural-specific enolase (Incstar, Inc.), microtubule associated protein 2 (MAP2, Boehringer Mannheim), glial fibrillary acidic protein, O4, or any other detectable marker specific to a neural progenitor, neuronal or glial cell.

Alternatively, expression of neural progenitor-specific, neural-specific or glial-specific markers is detected by conventional molecular biological techniques for amplifying and analyzing mRNA transcripts encoding any of the markers, such as but not limited to reverse transcriptase-mediated polymerase chain reaction (RT-PCR), transcription-mediated amplification (TMA), reverse transcriptase-mediated ligase chain reaction (RT-LCR), or hybridization analysis. Nucleic acid sequences encoding markers (e.g., nestin, neural RNA-binding protein Musashi, neurofilament M, neural-specific tubulin, neural-specific enolase, microtubule associated protein 2, glial fibrillary acidic protein, O4) specific to neural progenitor, neuronal or glial cells are known and available in databases such as GenBank. The skilled artisan can readily determine other useful marker-specific sequences for use as primers or probes by conducting a sequence similarity search of a genomics data base, such as the GenBank database of the National Center for Biotechnology Information (NCBI), using a computerized algorithm, such as PowerBLAST, QBLAST, PSI-BLAST, PHI-BLAST, gapped or ungapped BLAST, or the "Align" program through the Baylor College of Medicine server. (E.g., Aitchul, S. F., et al., *Gapped BLAST and PSI-BLAST: a new generation of protein database search programs*, Nucleic Acids Res. 25(17):3389-402 [1997]; Zhang, J., & Madden, T. L., *PowerBLAST: a new network BLAST application for interactive or automated sequence analysis and annotation*, Genome Res. 7(6): 649–56 [1997]); Madden, T. L., et al., *Applications of network BLAST server*, Methods Enzymol. 266:131–41 [1996]; Altschul, S. F., et al., *Basic local alignment search tool*, J. Mol. Biol. 215(3):403–10 [1990]).

Optionally, morphological criteria are additionally used to detect transdifferentiation of epidermal basal cells into neurons or neuron-like cells. For example, neurons or neuron-like cells may express neurites, or neurite-like processes, longer than three cell diameters (about 50 microns or longer).

The present invention also relates to a transdifferentiated cell of epidermal origin having a morphological, physiological and/or immunological feature of a neural progenitor, neuronal, or glial cell. The inventive cell can be, but is not necessarily, produced by the inventive method of transdifferentiating an epidermal basal cell into a cell having one or more morphological, physiological and/or immunological features of a neural progenitor, neuronal, or glial cell (astrocyte, oligodendrocyte, or microglia). The cell includes cultured cellular progeny of a cell transdifferentiated from an epidermal basal cell.

"Neural progenitor" is an ectodermally-derived pluripotent stem cell having, as a physiological feature, a capacity, under physiological conditions that favor differentiation (e.g., presence of particular neurotrophic factors), to develop one or more morphological, physiological and/or immunological features specifically associated with a neuronal or glial cell type, i.e., neurons, astrocytes (i.e., astroglia), oligodendrocytes (i.e., oligodendroglia), and microglia. For example, bipotent neural progenitor cells differentiate into astrocytes after exposure to ciliary neurotrophic factor (CNTF), or into neuronal cells after exposure to platelet-derived growth factor (PDGF). (E.g., J. K. Park et al., *Bipotent cortical progenitor cells process conflicting cues for neurons and glia in a hierarchical manner*, J. Neurosci.

19(23):10383–89 [1999]). Some neural progenitors are "neural restricted" progenitors, which can differentiate only into neurons.

The presence of neural progenitors can be detected by functional testing under suitable physiological conditions to determine the course of development and differentiation into neuronal or glial cells. Preferably, neural progenitor cells are identified by detecting the expression of any of several well-defined specific markers, such as the cytoskeletal protein nestin and/or neural RNA-binding protein Musashi (MSI). (E.g., T. Nagata et al., *Structure, backbone dynamics and interactions with RNA of the C-terminal RNA-binding domain of a mouse neural RNA-binding protein, Musashil*, J. Mol. Biol. 287(2):315–30 [1999]; P. Good et al., *The human Musashi homolog 1 (MSI1) gene encoding the homologue of Musashi/Nrp-1, a neural RNA-binding protein putatively expressed in CNS stem cells and neural progenitor cells*, Genomics 52(3):382–84 [1998]; S. Sakakibara et al., *Mouse-Musashi-1, a neural RNA-binding protein highly enriched in the mammalian CNS stem cell*, Dev. Biol. 176(2):230–42 [1996]).

"Neuronal" cells, or "neuron-like" cells, include cells that display one or more neural-specific morphological, physiological and/or immunological features associated with a neuronal cell type, including sensory neuronal, motoneuronal, or interneuronal cell types. The practitioner can choose, in connection with a particular application, the operative criteria or subset of specific features used for determining whether a transdifferentiated cell belongs to a particular type of neuronal population. Useful criterial features include morphological features (e.g., long processes or neurites); physiological and/or immunological features, such as expression of a set of neural-specific markers or antigens (e.g., neurofilament M, neural-specific β-tubulin, neural-specific enolase, microtubule associated protein 2, or others); synthesis of neurotransmitter(s) (e.g., doparnine; expression of tyrosine hydroxylase—the key enzyme in doparnine synthesis; or gamma aminobutyric acid [GABA]); the presence of receptors for neurotransmitter(s); and/or physiological features such as membrane excitability and/or developmental response to particular cytokines or growth factors. An advantage of the transdifferentiated cell(s) of the invention is that it can be manipulated, in vitro in the presence of specific exogenously supplied signal molecules, or in vivo within specific microenvironments, into diverse neuronal types as defined by the practitioner's operative criteria.

A glial cell or "glial-like" cell includes a cell that has one or more glial-specific features, associated with a glial cell type, including a morphological, physiological and/or immunological feature specific to a glial cell (e.g. astrocytes or oligodendrocytes), for example, expression of the astroglial marker fibrillary acidic protein (GFAP) or the oligodendroglial marker O4.

In one embodiment, the transdifferentiated cell exhibits a lack of mitotic activity under cell culture conditions which induce differentiation in neural progenitor cells, such as nutrient-rich medium containing neurotrophins (e.g., DMEM/F12, plus neuronal growth supplement B27 [Gibco-BRL], $10^{-7}$ M all-trans retinoic acid and brain derived neurotrophic factor [BDNF; 20 ng/mL], at 37° C. in an atmosphere containing 5% $CO_2$).

In other embodiments, the cell is a GABAergic cell, i.e., a cell that produces gamma aminobutyric acid, the predominant inhibitory neurotransmitter in the central nervous system. For example, treating the transdifferentiated cells plated on laminin coated surface with all trans retinoic acid ($10^{-7}$ M) and BDNF (10 ng/mL) for 5–15 days results in development of GABAergic neurons or neuron-like cells.

In still other embodiments, the transdifferentiated cell is a dopaminergic cell, i.e., a cell that produces dopamine, a catecholamine neurotransmitter and hormone. These cells result from post-transdifferentiation treatment with glial conditioned media and sonic hedgehog aminoterminal peptide.

In one embodiment, the transdifferentiated cell has a morphological, physiological and/or immunological feature of an glial cell, such as expression of glial fibrillary acidic rotein (GFAP).

It is a benefit of the inventive transdifferentiated cell(s) that they can be implanted into, and/or grafted to, a patient in need for use in cell therapy or gene therapy approaches to neurological injury or disease. Advantageously, the transdifferentiated cell(s) can be used directly without requiring a step for cell expansion.

The present invention also relates to a cell culture derived from the inventive transdifferentiated cell(s) originated from epidermal basal cells. The cell culture contains a plurality of cells that have a morphological, physiological and/or immunological feature of a neural progenitor, neuronal, or glial cell, for example, expression of one or more specific marker(s). The cell culture is maintained under culture conditions that favor the in vitro propagation of neural progenitors, neuronal, or glial cells, for example, suitable temperature, pH, nutrients, and growth factors, as known in the art. The cell culture can be manipulated to express additional or different neural-specific or glial specific-markers in the presence of specific exogenously supplied signal molecules.

The features and properties of the transdifferentiated cells and cell cultures of the present invention make them viable as a fundamental biotechnology tool directed to the human nervous system. Moreover, the transdifferentiated cells and cell cultures of the invention meet the technical criteria for use in cell and gene therapies directed to nervous system disease and disorders. First, the inventive transdifferentiated cells and cell cultures can display morphological and functional features of neurons: they can develop long neurites with a growth cones at the end, they express a number of neural specific genes; and they do not continue to proliferate in conditions which induce differentiation. Therefore, for use in gene therapy and cell therapy, the transdifferentiated cells can not only deliver a single potential gene or factor, but additionally are capable of furnishing the whole infrastructure for nerve regeneration.

Second, the cultured transdifferentiated cells can be propagated as multipotential nervous system progenitor cells in conditions that favor proliferation and do not induce differentiation. Hence, these progenitor cells retain the capacity to become many different types of neurons or neuron-like cells depending upon the environmental cues to which they are exposed, for example GABAergic or dopaminergic cells. This broad plasticity suggests that, once implanted, the cells of the present invention will retain the capacity to conform to many different host brain regions and to differentiate into neurons specific for that particular host region. These intrinsic properties of the transdifferentiated neurons are different from the existing tumorigenic cell lines, where some neuronal differentiation can be induced under artificial conditions.

Third, another advantage of the inventive transdifferentiated cells and cell cultures is that there is no need for cell expansion, as is required with stem cell technology used to generate neurons for cell and gene therapies. Thus, the transdifferentiated cells of the present invention are sufficient in number (several millions of cells) for direct implantation. In summary, the unique characteristics and properties of these transdifferentiated cells and cell cultures yield an invention of significant scientific and commercial potential.

Consequently, the present invention also relates to a method of delivering locally secretable regulatory factors in vivo within the nervous system of a mammalian subject, including a human. The method involves transdifferentiating a population of epidermal basal cells from the subject, in accordance with the inventive method described above, into cells having a morphological, physiological and/or immunological feature of a neuronal cell. Epidermal basal cells of the particular subject requiring treatment with secretable regulatory factors are preferred, in order to avoid transplant rejection. Before or after the transdifferentiation step, the cells are genetically modified, in vitro, with an expression vector comprising a DNA encoding a predetermined secretable regulatory factor, a biochemical precursor thereof or an enzyme that catalyzes the biosynthesis of either the factor or a precursor, and the genetically modified cells are selected, culted, and implanted into the subject. Enhanced secretion of the regulatory factor by the genetically modified cells results. This does not depend on the formation of functional interneuronal connections such as those that transmit electrochemical sensory, motor, or cognitive signals.

Examples of secretable regulatory factors include dopamine and neurotrophic factors, such as nerve growth factor (NGF), brain-derived growth factor (BDGF), neurotrophin-3, neurotrophin-4, insulin-like growth factor, ciliary neurotrophic factor (CNTF), or glia-derived neurotrophic factor. Nervous system disorders that can be treated using the method include Alzheimer's disease, diabetic neuropathy, taxol neuropathy, compressive neuropathy, AIDS related neuropathy, amyotrophic lateral sclerosis, large fiber neuropathy, vincristine neuropathy, and Parkinson's disease.

Genetically modifying the cells involves delivery of an expression vector comprising the DNA encoding the predetermined secretable regulatory factor, a precursor thereof, or an enzyme that catalyzes the biosynthesis of either the factor or a precursor. Expression of the gene for the regulatory factor, precursor, or enzyme is under the transcriptional control of a neuronal specific promoter (for example, neurofilament promoter or neural-specific enolase promoter).

Gene delivery to the cell is by any suitable in vitro gene delivery method. (E.g., D. T. Curiel et al., U.S. Pat. Nos. 5,521,291 and 5,547,932). Typically, gene delivery involves exposing a cell to a gene delivery mixture that includes preselected genetic material together with an appropriate vector, mixed, for example, with an effective amount of lipid transfecting agent (lipofection). The amount of each component of the mixture is chosen so that gene delivery to a specific species of cell is optimized. Such optimization requires no more than routine experimentation. The ratio of DNA to lipid is broad, preferably about 1:1, although other proportions may also be utilized depending on the type of lipid agent and the DNA utilized. This proportion is not crucial. Other well known gene delivery methods include electroporation or chemical methods. (E.g., M. Ostresh, *No barriers to entry: transfection tools get biomolecules in the door*, The Scientist 13(11):21–23 [1999]).

"Gene delivery agent", as used herein, means a composition of matter added to the genetic material for enhancing the uptake of exogenous DNA segment(s) into a mammalian cell. The enhancement is measured relative to the uptake in the absence of the gene delivery agent. Examples of gene delivery agents include adenovirus-transferrin-polylysine-DNA complexes. These complexes generally augment the uptake of DNA into the cell and reduce its breakdown during its passage through the cytoplasm to the nucleus of the cell.

An immunoliposome transfection method is a preferred means of gene delivery. Other preferred methods also yield high transfection efficiency, such as Ca-coprecipitation, or transfection using gene delivery agents such as Lipofectamine (Life Technologies), or Fugene-6 (Boehringer Mannheim, Inc.). Other preferred gene delivery agents include Lipofectin®, DMRIE C, Cellfectin® (Life Technologies), LipoTAXI (Stratagene), Superfect or Effectene (Qiagen). Although these are not as efficient gene delivery agents as viral agents, they have the advantage that they facilitate stable integration of xenogeneic DNA sequence into the vertebrate genome, without size restrictions commonly associated with virus-derived gene delivery agents. But a virus, or transfecting fragment thereof, can be used to facilitate the delivery of the genetic material into the cell. Examples of suitable viruses include adenoviruses, adeno-associated viruses, retroviruses such as human immune-deficiency virus, other lentiviruses, such as Moloney murine leukemia virus and the retrovirus vector derived from Moloney virus called vesicular-stomatitis-virus-glycoprotein (VSV-G)-Moloney murine leukemia virus, mumps virus, and transfecting fragments of any of these viruses, and other viral DNA segments that facilitate the uptake of the desired DNA segment by, and release into, the cytoplasm of cells and mixtures thereof. All of the above viruses may require modification to render them non-pathogenic or less antigenic. Other known viral vector systems are also useful.

Implantation of the genetically modified transdifferentiated cells is by conventional methods (e.g., stereotactic injection). Implantation is into an appropriate site within the nervous system of the subject, depending on the particular disorder being treated.

By way of example, the method is advantageous in the treatment of Parkinson's disease, which results mainly from degeneration of dopamine releasing neurons in the substantia nigra of the brain and the subsequent depletion of dopamine neurotransmitter in the striatum. The cause of this degeneration is unknown, but the motor degeneration symptoms of the disease can be alleviated by peripherally administering the dopamine precursor, L-dopa, at the early onset of the disease. As the disease continues to worsen, L-dopa is no longer effective, and currently, no further treatment is available. One promising treatment being developed is to transplant dopamine-rich substantia nigra neurons from fetal brain into the striatum of the brain of the patient. Results obtained from various clinical studies look extremely optimistic, however, it is estimated that up to 10 fetal brains are needed to obtain a sufficient number of cells for one transplant operation. This requirement renders unfeasible the wide application of the transplantation of primary fetal neurons as a therapeutic treatment modality. This problem is resolved, however, by utilizing the transdifferentiated neurons or neuron-like cells of the present invention for treatment of Parkinson's disease.

It is now widely recognized that transplantation of doparnine producing cells is the most promising therapy of treating severe Parkinson's disease. Stable cell populations or cell lines genetically modified to produce doparnine is essential to an effective therapy. Since tyrosine hydroxylase (TH) is the key enzyme for dopamine biosynthesis, cloning the TH gene into an appropriate expression vector is a first step in the method of treatment. Human TH cDNA is cloned into a eukaryotic expression vector. After gene delivery, clones of genetically modified cells that demonstrate stable integration of the expression vector are selected for implantation purposes. Thus, transdifferentiated cells of the present invention are produced with enhanced expression of the tyrosine hydroxylase (TH) gene.

These cells are implanted into the patient's striatum or brain. The cells are typically implanted bilaterally in the caudate nucleus and putamen by using Magnetic Resonance Imaging (MRI)-guided stereotactic techniques. A stereotactic frame is affixed to the skull after administration of local anesthesia. The caudate nucleus and putamen are then visualized with MRI. Thereafter, under general anesthesia, about 10 passes with very thin stereotactic needles are made bilaterally, 4 mm apart in the caudate and putamen. The rationale for track spacing at approximately 4 mm intervals is important because fetal dopamine neuron processes grow several millimeters, reinnervating the host's striatum. Four trajectories for needle tracks in the caudate and six tracks in the putamen are calculated to avoid the posterior limb of the internal capsule. The entry points for the putamnen and caudate tracks are at two different sites on the surface of the brain. The tracks to the putamen are approximately vertical with reference to a coronal plane, while the approach to the caudate is at an angle of approximately 30 degrees. After the implantation surgery, the implanted cells secrete dopamine in situ alleviating the subject's Parkinson's disease symptoms.

The present invention also relates to a method of identifying a novel nerve growth (or neurotrophic) factor that employs transdifferentiated cells of the invention. The methods involve transdifferentiating a population of proliferating epidermal basal cells into neuronal progenitor cells, neuronal cells, or glial cells; culturing the transdifferentiated cells; exposing the cultured cells, in vitro, to a potential nerve growth factor; and detecting the presence or absence of an effect of the potential nerve growth factor on the survival of the cells or on a morphological or electrophysiological characteristic and/or molecular biological property of the cells. The transdifferentiated cells are assayed in vitro to determine whether there is an effect of a potential nerve growth factor on a physiological or molecular biological property of the transdifferentiated cells. For example, which, if any, neuronal or glial cell types develop from neural progenitors, the maturation of particular cell types, and the continued support of cell survival (e.g., effect on cell numbers) can be determined. In addition, experimental techniques, based on an electrophysiological characteristic (patch clamp, different types of intracellular recording, etc.) or molecular biological properties (gene expression profiles, organization of cytoskeleton, organization of ion channels and receptors etc.) can be used to detect the effects of potential nerve growth/neurotrophic factors on particular cell types. The potential factor can be, but need not be an isolated compound; the inventive transdifferentiated cells can be used to test, or assay, the effect, or lack thereof, of potential growth factor sources (tissue homogenates, expression cDNA library products, etc.) on the survival and functional characteristics of the cells to detect candidates for further isolation.

The use of transdifferentiated epidermal basal cells bypasses the difficulties in isolating and culturing neuronal cell types from the brain, and, therefore, the inventive method of identifying a novel nerve growth factor is a benefit to research in this area.

This same advantage pertains to the inventive method of using cells transdifferentiated from epidermal basal cells to identify a potential chemotherapeutic agent by transdifferentiating a population of epidermal basal cells into neuronal progenitor, neuronal, or glial cells by the inventive method described above; culturing the transdifferentiated cells; exposing the cultured cells, in vitro, to a potential chemotherapeutic agent; and detecting the presence or absence of an effect of the potential chemotherapeutic agent on the survival of the cells or on a morphological or electrophysiological characteristic and/or molecular biological property of said cells. An effect altering cell survival, a morphological or electrophysiological characteristic and/or a molecular biological property of the cells indicates the activity of the chemotherapeutic agent. The potential chemotherapeutic agent can be an agent intended to treat a nervous system disorder, or the method can be used to test an agent intended or proposed for treating any other type of disorder for its effects on cells possessing neural progenitor, neuronal or glial cell features. Experimental assay techniques, based on an electrophysiological characteristic (patch clamp, different types of intracellular recording, etc.) or molecular biological properties (gene expression profiles, organization of cytoskeleton, organization of ion channels and receptors etc.), as well as cell survival, can be used to detect the effects of potential chemotherapeutic agents on particular cell types. The potential chemotherapeutic agent can be, but need not be an isolated compound; the inventive transdifferentiated cells can be used to test, or assay, the effect of potential chemotherapeutic agents (tissue homogenates, expression cDNA library products, etc.) on the survival and functional characteristics of the cells to detect candidates for further isolation and development. Since epidermal basal cells transdifferentiated into neurons or neuron-like cells in culture can express several neurotransmitters and receptor complexes, cell lines derived from these cells can be developed which, when differentiated into mature neurons, would display a unique profile of neurotransmitter receptor complexes. Such neuronal cell lines can be valuable tools for designing and screening potential chemotherapeutic agents.

The present invention also relates to a method of using transdifferentiated cells or cell cultures to screen a potential chemotherapeutic agent to treat a nervous system disorder of genetic origin, for example, Alzheimer's disease. The method is practiced in accordance with the above-described method of screening a potential chemotherapeutic agent, however, epidermal basal cells derived from a human subject diagnosed with a particular nervous system disorder of genetic origin are transdifferentiated and the effect of the potential chemotherapeutic agent on a physiological or molecular biological property of the transdifferentiated cells is assayed in vitro. Different types of neuronal cells derived from transdifferentiated epidermal basal cells of the present invention will provide novel methodologies to screen potential chemotherapeutic agents. For example, using the epidermal basal cells from patients with genetic defects that affect the nervous system will make it possible to manipulate environmental cues to induce the development of various types of neuronal cell populations that also carry this genetic defect. These cells can be used for screening of chemotherapeutic agents which potentially have effect on the diseased neurons or neuron-like cells displaying a specific set or profile of neurotransmitters, receptors complexes, and ion channels.

Regardless of whether under a particular set of environmental conditions, in vitro, the inventive transdifferentiated cells express all the biochemical, morphological, and functional characteristics of a given neuronal population in vivo, they provide at least useful simulations of neurons for identifying, screening, or isolating promising new drugs or neural growth factors. Once the potential of a chemical agent is identified by the inventive methods, then, further research can be done to verify its actual effect on particular cell populations of the nervous system and ascertain its clinical usefulness. Thus, the inventive methods of screening a potential chemotherapeutic agent are of benefit in finding and developing the next generation of pharmaceutical drugs narrowly aimed at modifying specific brain functions.

In summary, the epidermal basal cell transdifferentiation technology of the present invention offers broad and significant potentials for treating nervous system disorders in both the areas of cell and gene therapy, as well as offering a potential new source of human neural progenitor cells, neurons, glial cells or neuron-like or glial-like cells for research and drug screening.

The present invention also relates to a kit for transdifferentiating an epidermal basal cell into a cell having one or more morphological, physiological and/or immunological feature(s) of a neural progenitor, neuronal, or glial cell. The kit is an assemblage of materials for facilitating the transdifferentiation of epidermal basal cells in accordance with the inventive methods. A kit of the present invention comprises an antagonist of bone morphogenetic protein (BMP), such as fetuin, noggin, chordin, gremlin, or follistatin, and at least one antisense oligonucleotide comprising a segment of a human MSX1 gene, a segment of a human HES1 gene, or a non-human homologous counterpart of either of these. The kit can further contain a retinoid compound, such as all trans-retinoic acid or Vitamin A, and, optionally a nerve growth factor or neurotrophin, such as BDNF, CNTF, PDGF, NGF, NT-3, NT-4, or sonic hedgehog, as described above.

The materials or components assembled in the inventive kit can be provided to the practitioner stored in any convenient and suitable ways that preserve their operability and utility. For example the components can be in dissolved, dehydrated, or lyophilized form; they can be provided at room, refrigerated or frozen temperatures. The kits of the present invention preferably include instructions for using the materials or components effectively for practicing any or all of the inventive methods.

The foregoing descriptions of the methods, transdifferentiated cells, cell cultures, and kits of the present invention are illustrative and by no means exhaustive. The invention will now be described in greater detail by reference to the following non-limiting examples.

EXAMPLES

Example 1

Methods
Preparation of Epidermal Cell Culture and Dedifferentiation of Cell Population.

Human adult skin was obtained from surgery procedures or skin biopsy. Before cultivation, as much as possible of the subepidermal tissue was removed by gentle scraping. Primary cultures were initiated by culturing 4–10 2×2 mm explants/35 mm tissue culture dish in Dulbecco's modified Eagle medium (DMEM; GIBCO-BRL, Life Technologies, Inc.) with 15% fetal calf serum (GIBCO-BRL, Life Technologies, Inc.), 0.4 $\mu$g/mL hydrocortisone, and 10 ng/mL epidermal growth factor (EGF; Collaborative Research, Inc.). The medium was changed every three days. Thirty to thirty-five day old cultures were used for subsequent experimentation. Differentiated keratinized cell layers were stripped off by incubating the cultures in $Ca^{2+}$-free minimal essential medium (SMEM; GIBCO-BRL, Life Technologies, Inc.). After 72 hours in calcium-free medium, suprabasal layers were detached and removed by aseptic aspiration after shaking of the culture dish. Thus, this calcium free treatment dedifferentiated the cell population by removing from the population of epidermal basal cells the overlayer of cells expressing cytokeratines. All cell cultures were incubated in 6-well tissue culture plates at a plating density of about 50,000 cells per well, at 37° C. in an atmosphere containing 5% $CO_2$.

Antagonism BM Signal Transduction and Transdifferentiation.

After aspiration of the kertinized cells, the epidermal basal cells were then incubated in DMEM/F12 with normal $Ca^{2+}$ concentration (2 mM) (DMEM, GIBCO) supplemented according to the manufacturer's instructions with neuronal growth supplement B27 (Gibco-BRL), $10^{-7}$ M all-trans retinoic acid and brain derived neurotrophic factor (BDNF; 20 ng/mL) and different concentrations of bovine fetuin (10–7 to $5 \times 10^{-5}$M, Sigma) and human MSX1 and/or human HES1 antisense oligonucleotides. Fetuin and antisense oligonucleotides were present for the next three days and then were removed from culture media and replaced with fresh medium containing all the components except anti sense oligonucleotides. After three more days, the fetuin-containing medium was replaced with fresh medium minus fetuin, but containing all-trans retinoic acid and BDNF.

Preparation and Use of Antisense Oligonucleotides.

Two human MSX1-targeting antisense oligonucleotides sequences were synthesized:

(1) 5'-GACACCGAGTGGCAAAGAAGTCATGTC-3' (first methionine; MSX1-1; SEQ. ID. NO.:1); and (2) 5'-CGGCTTCCTGTGGTCGGCCATGAG-3' (third methionine; MSX1-2; SEQ. ID. NO.:2).

Additionally, human full length HES1 cDNA from the human fetal brain cDNA library was isolated and sequenced (Stratagene). Two HES1-targeting anti sense oligonucleotides were synthesized, corresponding to:

(1) the human HES1 open reading frame 5' sequence 5'-ACCGGGACGAGGAATTTTTCTCCATFATATCAGC-3' (HES1-1; SEQ. ID. NO.:3); and (2) the human HES1 middle sequence 5'-CACGGAGGTGCCGCTGTTGCTGGGCTGGTGTGGTGTAGAC-3' (HES1-2; SEQ. ID. NO.:4).

The MSX1 and HES1 antisense oligonucleotides were synthesized and thio-modified to order by Sigma/Genesis. Antisense oligonucleotides were directly added to the culture media at the concentration of 5 $\mu$M. Randomly synthesized oligonucleotides and oligonucleotides corresponding to the sequence of human albumin were used as controls.

Analytical Method to Detect Transdifferentiation.

Immunohistochemical detection of neurofilament M expression was chosen as one marker for neuronal differentiation Ten days after initiation of transdifferentiation cells were fixed with 4% paraformaldehyde and processed according to the immunohistochemical detection protocol recommended by the antibody manufacturer (Sigma, Inc.). Cells expressing Neurofilament M were counted by fluorescent microscopy. Five to seven fields of immuno-stained cells were counted, each field containing 100–300 cells.

Example 2

Transdifferentiation of Epidermal Basal Cells

Different treatment combinations were tested including fetuin (to antagonize or inhibit endogenous BMP signal transduction activity) with or without MSX1 and/or HES1 antisense oligonucleoddes (to suppress MSX1 and HES1 expression) to demonstrate transdifferentiation of epidermal basal cells into neuronal or neuron-like cells. After a 3-day treatment with the various combinations of fetuin and/or antisense oligonucleotides, cells in all treatment groups were grown in the presence of all-trans retinoic acid ($10^{-7}$ M) and BDNF (20 ng/mL) for 7 additional days before immunostaining for the neural-specific antigen neurofilament M. The values in Table 1 show the relative effectiveness of the various treatments.

The results in Table 1 demonstrate that transdifferentiation of epidermal basal cells into Neurofilament M positive cells requires antagonism of BMP signal transduction by fetuin in combination with suppression of MSX1 and/or HES1 gene expression. The two treatment combinations that were most effective in producing transdifferention of epidermal basal cells were those that combined fetuin and antisense oligonucleotides directed to suppressing the expression of both MSX1 and HES1 (22–27% of the treated cells), about 30 to 50-fold more effective than treatment with fetuin and antisense oligonucleotides targeting either MSX1 or HES1. Fetuin alone or antisense oligonucleotides alone did not result in transdifferentiation. Controls treated in the first three days with randomly synthesized oligonucleotides or oligonucleotides corresponding to the sequence of human albumin also failed to produce transdifferentiation of epidermal basal cells (not shown in Table 1).

Figure 1A:
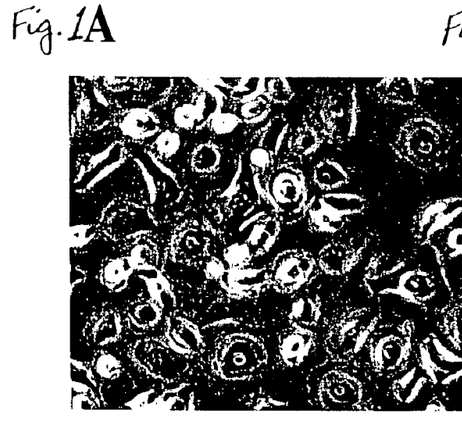
FIG. 1(A) shows epidermal basal cells immediately after treatment with calcium-free medium, and before exposing the cells to antisense oligonucleotides and fetuin.
Figure 1B:
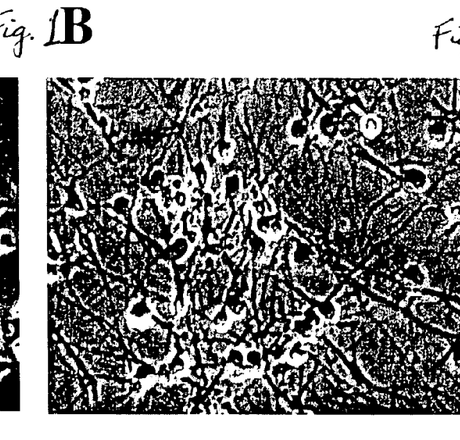
FIG. 1(B) shows transdifferentiated cells that have developed neurite-like morphological structures characteristic of neuronal cells after treatment with fetuin, antisense oligonucleotides targeting MSX1 and HES1, all-trans retinoic acid and BDNF.
Figure 1C:
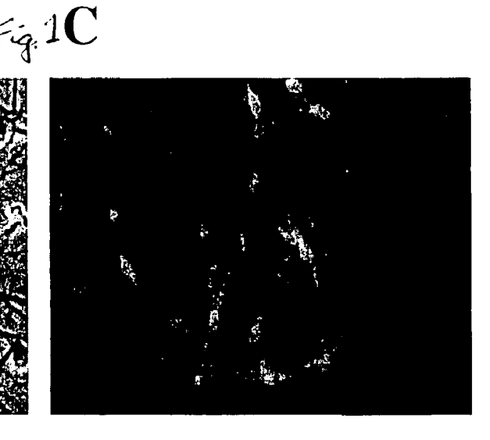
FIG. 1(C) shows expression by transdifferentiated cells of Neurofilament-M as detected by immunofluorescent staining. Magnification is 500×.

Transdifferentiation of epidermal basal cells receiving the fetuin +MSX1 -1+MSX1-2 +HES1-1+HES1-2 treatment, as described above, is demonstrated micrographically in FIG. 1. FIG. 1(A) shows epidermal basal cells immediately after treatment with calcium-free medium, and before exposing the cells to fetuin and MSX1- and HES1-targeting antisense oligonucleotides. FIG. 1(B) shows transdifferentiated cells developed neurite-like morphological structures resembling those of neuronal cells. FIG. 1(C) demonstrates the expression by transdifferentiated cells of Neurofilament-M, as detected by immunofluorescent staining. Epidermal basal cell controls did not bind the Neurofilament-M-specific antibodies (data not shown).

TABLE 1

Transdifferentiation of Epidermal Basal Cells

| Treatment (addition to medium) | % of cells expressing Neurofilament M |
|---|---|
| control, no addition | 0 |
| fetuin | 0 |
| MSX1-1 | 0 |
| MSX1-2 | 0 |
| HES1-1 | 0 |
| HES1-2 | 0 |
| MSX1-1 + MSX1-2 + HES1-1 + HES1-2 | 0 |
| fetuin + MSX1-1 + MSX1-2 | 0.5 |
| fetuin + HES1-1 + HES1-2 | 0.8 |
| fetuin + MSX1-1 + HES1-1 | 22 |
| fetuin + MSX1-1 + MSX1-2 + HES1-1 + HES1-2 | 27 |

Example 3

Efficiency of Transdifferention Depends on the Concentration of BMP-antagonist

Figure 2:
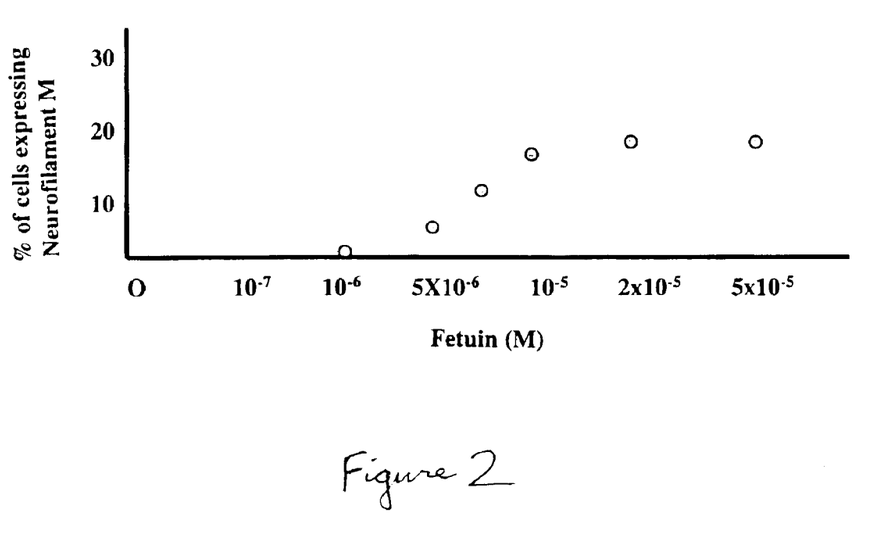

FIG. 2 illustrates that suppression of BMP signal transduction to allow expression of neuronal characteristics is concentration dependent with respect to the BMP antagonist. At a concentration in the medium of $1 \times 10^{-5}$ to $5 \times 10^{-5}$ M, fetuin had maximal effect on the expression of neurofilament M by transdifferentiated cells (FIG. 2).

The foregoing example being illustrative but not an exhaustive description of the embodiments of the present invention, the following claims are presented.

We claim:

1. An in vitro method of transdifferentiating an epidermal basal cell having one or more morphological, physiological and/or immunological feature(s) of a neuronal cell, comprising:
   (a) culturing a proliferating epidermal basal cell population comprising one or more epidermal basal cell(s), said cell(s) derived from the skin of a mammalian subject;
   (b) exposing the cell(s) to an amount of fetuin, noggin, chordin gremlin or follistatin antagonist of bone morphogenetic protein (BMP) effective to antagonize endogenous BMP signal transduction activity;
   (c) growing the cell(s) in the presence of at least one antisense oligonucleotide comprising a segment of a human MSX1 gene and/or a segment of a human HES1 gene, in an amount effective to suppress the expression of functional gene product of MSX1 or HES1, whereby the cell is transdifferentiated into a cell having one or more morphological, physiological and/or immunological feature(s) of a neuronal cell; and
   (d) growing the transdifferentiated cell in a medium comprising a retinoid compound and a signal molecule selected from the group consisting of brain-derived neurotrophic factor (BDNF), platelet-derived growth factor (PDGF), nerve growth factor (NGF), sonic hedgehog, sonic hedgehog aminoterminal peptide, neurotrophin (NT)-3, and neurotrophin (NT)-4; and
   wherein the physiological and/or immunological feature comprises expression of a neuronal cell marker selected from the group consisting of neurofilament M, neural-specific β-tubulin, neural-specific enolase, and microtubule associated protein 2, or a combination of any of these; and wherein the morphological feature comprises one or more morphological neurite-like process(es) at least about 50 micrometers in length.

2. The method of claim 1, wherein the subject is a human.

3. The method of claim 1, wherein the epidermal basal cell(s) is derived from a skin biopsy.

4. The method of claim 1, wherein culturing the proliferating epidermal basal cell population further comprises separating keratinized epidermal cells from the epidermal basal cells in a calcium-free medium.

5. The method of claim 1, wherein the amount of the antagonist of bone morphogenetic protein is about $10^{-6}$ to $10^{-4}$ M.

6. The method of claim 5, wherein the amount of the antagonist of bone morphogenetic protein is about $5 \times 10^{-6}$ to $5 \times 10^{-5}$ M.

7. The method of claim 1, wherein the fetuin is mammalian or avian fetuin.

8. The method of claim 7, wherein the mammalian fetuin is human, bovine, porcine, ovine, or equine fetuin.

9. The method of claim 1, wherein the antisense oligonucleotide(s) is modified with one or more thio groups.

10. The method of claim 1, wherein the amount of the antisense oligteotide is about $5 \times 10^{-6}$ M to about $10^{-5}$ M.

11. The method of claim 1, wherein the retinoid compound is all-trans retinoic acid or Vitamin A.

12. A kit for transdifferentiating, in vitro, an epidermal basal cell into a cell having one or more morphological, physiological and/or immunological feature(s) of a neuronal cell, comprising:
   (A) a fetuin, noggin, chordin, gremlin or follistatin antagonist of bone morphogenetic protein (BMP); and
   (B) at least one antisense oligonucleotide comprising a segment of a human MSX1 gene, and/or a segment of a human HES1 gene, and
   (C) a retinoid compound and a signal molecule selected from the group consisting of brain-derived neurotrophic factor (BDNF), platelet-derived growth factor (PDGF), nerve growth factor (NGF), neurotrophin (NT)-3, neurotrophin (NT)-4, sonic hedgehog, and sonic hedgehog aminoterminal peptide.

13. The kit of claim 12, further comprising instructions for using (A) and (B) in transdifferentiating a subject's epidermal basal cell(s).

14. The kit of claim 12, wherein the retinoid compound is all-trans retinoic acid or Vitamin A.

15. An in vitro method of transdifferentiating an epidermal basal cell into a cell having one or more morphological, physiological and/or immunological feature(s) of a neuronal cell, comprising:

(a) culturing a proliferating epidermal basal cell population comprising one or more epidermal basal cell(s), said cell(s) derived from the skin of a mammalian subject;

(b) exposing the cell(s) to an amount of a fetuin, noggin, chordin, gremlin or follistatin antagonist of bone morphogenetic protein (BMP) effective to antagonize endogenous BMP signal transduction activity;

(c) growing the cell(s) in the presence of at least one antisense oligonucleotide comprising a segment of a human MSX1 gene and/or a segment of a human HES1 gene, in an amount effective to suppress the expression of functional gene product of MSX1 and/or HES1, whereby the cell is transdifferentiated into a cell having one or more morphological, physiological and/or immunological feature(s) of a neuronal cell; and (d) growing the transdifferentiated cell in a medium comprising a retinoid compound and a signal molecule selected from the group consisting of brain-derived neurotrophic factor (BDNF), platelet-derived growth factor (PDGF), nerve growth factor (NGF), neurotrophin (NT)-3, and neurotrophin (NT)-4;

wherein the physiological and/or immunological feature comprises expression of a neuronal cell marker selected from the group consisting of neurofilament M, neuro-specific β-tubulin, neural-specific enolase, and microtubule associate protein 2, or a combination of any of these; and wherein the morphological feature comprises one or more morphological neurite-like process(es) at least about 50 micrometers in length.

16. The method of claim 15, wherein the subject is a human.

17. The method of claim 15, wherein the epidermal basal cell(s) is derived from a skin biopsy.

18. The method of claim 15, wherein culturing the proliferating epidermal basal cell population further comprises separating keratinized epidermal cells from the epidermal basal celled in a calcium-free medium.

19. The method of claim 15, wherein the amount of the antagonist of bone morphogenetic protein is about $10^{-6}$ to $10^{-4}$M.

20. The method of claim 19, wherein the amount of the antagonist of bone morphogenetic protein is about $5\times10^{-6}$ to $5\times10^{-5}$M.

21. The method of claim 15, wherein the fetuin is mammalian or avian fetuin.

22. The method of claim 21, wherein the mammalian fetuin is human, bovine, porcine, ovine, or equine fetuin.

23. The method of claim 15, wherein the antisense oligonucleotide(s) is modified with one or more thio groups.

24. The method of claim 15, wherein the amount of the antisense oligonucleotide is about $5\times10^{-6}$M to about $10^{-5}$M.

25. The method of claim 15, wherein the retinoid compound is all-trans retinoic acid or Vitamin A.

* * * * *

SEQUENCE LISTING

<160> NUMBER OF SEQ ID NOS: 4

<210> SEQ ID NO 1
<211> LENGTH: 27
<212> TYPE: DNA
<213> ORGANISM: Homo sapiens
<220> FEATURE:
<221> NAME/KEY: gene
<222> LOCATION: (0)...(0)
<223> OTHER INFORMATION: MSX1 antisense oligonucleotide sequence MSX1-1

<400> SEQUENCE: 1
gacaccgagt ggcaaagaag tcatgtc                27

<210> SEQ ID NO 2
<211> LENGTH: 24
<212> TYPE: DNA
<213> ORGANISM: Homo sapiens
<220> FEATURE:
<221> NAME/KEY: gene
<222> LOCATION: (0)...(0)
<223> OTHER INFORMATION: MSX1 antisense oligonucleotide sequence MSX1-2

<400> SEQUENCE: 2
cggcttcctg tggtcggcca tgag                24

-continued

```
<210> SEQ ID NO 3
<211> LENGTH: 35
<212> TYPE: DNA
<213> ORGANISM: Homo sapiens
<220> FEATURE:
<221> NAME/KEY: gene
<222> LOCATION: (0)...(0)
<223> OTHER INFORMATION: HES1 open reading frame 5' sequence (HES1-1)

<400> SEQUENCE: 3
accggggacg aggaattttt ctccattata tcagc                                  35

<210> SEQ ID NO 4
<211> LENGTH: 40
<212> TYPE: DNA
<213> ORGANISM: Homo sapiens
<220> FEATURE:
<221> NAME/KEY: gene
<222> LOCATION: (0)...(0)
<223> OTHER INFORMATION: HES1 open reading frame middle sequence
      (HES1-2)

<400> SEQUENCE: 4
cacggaggtg ccgctgttgc tgggctggtg tggtgtagac                             40
```